(12) United States Patent
Dawidowski et al.

(10) Patent No.: US 8,318,987 B2
(45) Date of Patent: Nov. 27, 2012

(54) PROCESS FOR THE PREPARATION OF LITHIUM ALCOHOLATE SOLUTIONS

(75) Inventors: Dirk Dawidowski, Friedberg (DE); Ulrich Wietelmann, Friedrichsdorf (DE); Peter Rittmeyer, Sulzbach/Taunus (DE)

(73) Assignee: Chemetall GmbH, Frankfurt (DE)

( * ) Notice: Subject to any disclaimer, the term of this patent is extended or adjusted under 35 U.S.C. 154(b) by 279 days.

(21) Appl. No.: 12/669,223

(22) PCT Filed: Jul. 31, 2008

(86) PCT No.: PCT/EP2008/060036
§ 371 (c)(1),
(2), (4) Date: Jan. 15, 2010

(87) PCT Pub. No.: WO2009/016217
PCT Pub. Date: Feb. 5, 2009

(65) Prior Publication Data
US 2010/0185025 A1     Jul. 22, 2010

(30) Foreign Application Priority Data

Jul. 31, 2007 (DE) .................. 10 2007 036 275

(51) Int. Cl.
*C07C 31/30* (2006.01)
*C07C 29/70* (2006.01)
(52) U.S. Cl. ........................................ 568/851; 568/902
(58) Field of Classification Search .................. 568/851, 568/902
See application file for complete search history.

(56) References Cited

U.S. PATENT DOCUMENTS

| 3,971,833 A | 7/1976 | Lenz et al. |
| 5,276,219 A | 1/1994 | Schwindeman et al. |
| 5,583,269 A | 12/1996 | Morrison et al. |
| 6,194,617 B1 | 2/2001 | Morrison et al. |

FOREIGN PATENT DOCUMENTS

EP    0 721 445    12/1999

OTHER PUBLICATIONS

Smith "Preparation of Tert-Butyllithium", *J. Organ. Chem.* 82 (1974) pp. 1-6.

*Primary Examiner* — Brian J Davis
(74) *Attorney, Agent, or Firm* — Fulbright & Jaworski LLP

(57) ABSTRACT

The present invention relates to a process for the preparation of lithium alcoholates solution.

14 Claims, No Drawings

PROCESS FOR THE PREPARATION OF LITHIUM ALCOHOLATE SOLUTIONS

This application is a §371 of PCT/EP2008/060036 filed Jul. 31, 2008 and claims priority from DE 10 2007 036 275.9 filed Jul. 31, 2007.

The subject matter of the present invention is a process for the preparation of lithium alcoholate solutions.

Alkali-metal alcoholates are used in organic synthesis as bases for the preparation of intermediate products and fine chemicals. These have a use, for example, as pharmaceutical, agricultural and also aroma and flavouring substances.

Lithium alcoholates can be prepared by reacting organolithium compounds with alcohols in accordance with:

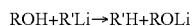

Another method which is more favourable commercially is based on metallic lithium instead of organolithium compounds:

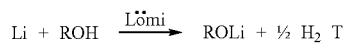

This reaction is as a rule carried out in organic solvents (Lömi) which must be inert with respect to Li metal. Aprotic organic compounds, such as ether (e.g. diethyl ether, THF, dibutyl ether, ethylene glycol dialkyl ether), aromatic hydrocarbons (benzene, toluene, ethyl benzene, cumene etc.) or saturated hydrocarbons (e.g. pentane, hexane, heptane, paraffin oils) are suitable as such solvents.

In principle, the lithium metal can be present in a molten or solid form. The use of molten metal, however, on account of its high melting point of 180.5° C. as a rule requires an operation under increased pressure (U.S. Pat. No. 3,971,833). The disadvantage of this technique accordingly is the safety risk on account of the extreme reactivity of molten lithium and also the comparatively high investment costs for pressure-resistant systems.

If solid lithium metal is used, the reactivity is greatly reduced in particular with respect to secondary and tertiary alcohols, that is, the reaction times are often considerably extended, and this has negative effects upon the economic efficiency of the process. In order to increase the reaction rate, the following possibilities are known:

Use of lithium of finely divided quality and an excess of alcohol. U.S. Pat. No. 5,276,219 thus describes the preparation of lithium tert-butoxide as a solution in THF with finely dispersed lithium (<300 μm) at reflux temperatures (approximately 66° C.) with the use of an excess of alcohol of at least 5 to 20% (or 100%). Commercially available metal with an Na content of approximately 0.4-0.76% is used as the lithium grade. Other polar solvents (ethers or amines) can also be used instead of THF. The advantage of the process is that clear or easily filterable product solutions develop. The disadvantage is that the product solutions are contaminated by free alcohol.

Use of an excess of Na-deficient Li-metal in coarse pieces. U.S. Pat. No. 5,583,269 (EP 721445) thus describes a method for the preparation of lithium tert-butoxide, characterised in that lithium metal with an Na content of a maximum of 0.1% in a formation of at least 1 cm³/piece is reacted with a tertiary alcohol in a solvent selected from ethers or hydrocarbons. The molar ratio lithium:alcohol lies between 2:1 and 10:1, and the reaction temperature lies between 34.6 and 100° C. The disadvantage of this process lies in the fact that only when a sufficiently high excess of lithium is used can economically acceptable reaction times be realized. The volume that is taken up by the excess lithium detracts from the specific product quantity (1 product per 1 reactor volume). Moreover, in the case of the last run of an operation a comparatively large amount of lithium remains over, which has to be disposed of in an expensive way or deactivated, for example with water.

A further disadvantage of the two processes described above presents itself when the synthesis is carried out in THF, a solvent which is "prescribed as being mandatory" in U.S. Pat. No. 5,276,219. Lithium metal reacts with THF with ring opening, as a result of which an insoluble, extremely finely dispersed solid matter develops that makes the product solutions practically unfilterable. As a result, the separation of excess lithium is rendered very difficult or made impossible. Moreover, the insoluble turbid substances often constitute a disturbance in subsequent applications in organic synthesis. Furthermore, the solubility of lithium alcoholates in THF is very limited; for example, the saturation concentration of LTB amounts to only approximately 20%.

The object of the present invention consists in developing a process which overcomes the disadvantages of the prior art, in particular in providing a process which delivers easily filterable solutions of Li salts of secondary and tertiary alcohols in an organic solvent that contain as far as possible no or only a maximum of 10 molar % free alcohol. The process is to render possible short reaction times and is not to have to rely on the use of high lithium excesses, that is, it should be possible to manage with Li excesses of a maximum of 100%.

The underlying object of the invention is achieved in accordance with the invention in that lithium metal with a maximum Na content of 0.2% in an aprotic solvent or solvent mixture is brought into contact with a secondary or tertiary alcohol. Lithium metal is preferably used that has an Na content of a maximum of 0.1, particularly preferably maximally less than 0.05%, especially preferably less than 0.01%. The lithium metal is used in formations of <0.5 ml, preferably <0.1 ml, particularly preferably <0.01 ml per piece. The lithium metal is present in an excess of a minimum of 1%, a maximum of 100%, preferably in an excess of 5 to 30%, relative to the total quantity of alcohol.

In accordance with the invention, saturated or unsaturated hydrocarbons or acyclic ethers or mixtures thereof are used as the aprotic solvent. In accordance with the invention, preferred solvents are: pentane, hexane, heptane, octane, methyl cyclohexane or industrial boiling sections, such as, for example, industrial hexanes, paraffin oils (white oils) or the like; benzene, toluene, ethyl benzene, xylenes, cumene or the like; diethyl ether, methyl tert-butyl ether, dipropyl ether, dibutyl ether, diphenyl ether and the like and also mixtures of at least two of the compounds mentioned.

In a preferred variant of the preparation, the lithium metal is placed in the aprotic solvent and mixed, whilst stirring, with the desired secondary or tertiary alcohol. The reaction temperature generally lies between 0 and 150 ° C., preferably 20-100° C., particularly preferably at 30 ° C. up to the boiling point of the solvent or solvent mixture used. The metering time for the alcohol is dependent on the reactivity of the respective alcohol ROH (generally the reactivity drops with the bulkiness of the remainder R, that is, secondary alcohols react more quickly than tertiary alcohols), the temperature and the surface area of the metallic lithium at the respective point in time. Generally, the metering time lies between 10 min and 20 hours, preferably 1-10 hours.

It has been found surprisingly that the necessary reaction time is dependent on the Na content of the lithium used and that the reaction runs all the more quickly, the lower the Na content is. This is surprising for the person skilled in the art in so far as sodium generally activates the lithium for reactions, for example in hydrocarbons (W. N. Smith Jr. *J. Organomet. Chem.* 82, 1974, 1-6). Certainly for the case of the Li/THF/tert-butanol system acceleration of the reaction as a result of a decreasing Na content is known (U.S. Pat. No. 5,583,269), yet this is a quite specific effect that goes back to the splitting (ring opening) of the 5-ring THF by lithium. Since according to the present process in accordance with the invention no cyclic ethers are used, it is not logical to expect a retarding effect by sodium.

It has, however, been observed that the reaction rate at the start of a run is largely independent of the Na content, yet decreases greatly in the course of the reaction. This effect goes back to the fact that the lithium particles become lumpy as a function of the Na content at differing rates and to differing extents. As a result, the Li surface area might possibly decrease greatly so that extremely long reaction times are required. Only when there is a fall below an Na content of 0.2, preferably 0.1, particularly preferably 0.05, especially preferably 0.01%, is there no longer any significant tendency to agglomerate/become lumpy. Consequently, synthesis runs with low-Na lithium metal only require a fraction of the reaction times compared with such runs that are carried out with "industrial Li metal", that is, such a metal with a ≧0.2% Na content.

The process in accordance with the invention is especially suitable for preparing lithium tert-butoxide, lithium tert-amoxide and lithium isopropoxide in hexane or heptane-containing solvents.

The invention claimed is:

1. A process for the preparation of lithium alcoholate solutions in an aprotic solvent or solvent mixture, wherein a secondary or tertiary alcohol is reacted with an excess of lithium metal which has a sodium content of a maximum of 0.2 wt. %, wherein the lithium metal is present in particles with a volume of a maximum of 0.5 ml.

2. A process according to claim 1, wherein the lithium metal has Na contents of a maximum of 0.1 wt. %.

3. A process according to claim 1, wherein the lithium metal is present in particles with a volume of a maximum of 0.1 ml.

4. A process according to claim 1, wherein the lithium metal is present in an excess of 1-100 wt. %.

5. A process according to claim 1, wherein the solvent is a saturated hydrocarbon or an aromatic hydrocarbon.

6. A process according to claim 1, wherein the solvent is an acyclic ether.

7. A process according to claim 1, wherein the reaction is carried out at temperatures of 0-150° C.

8. A process according to claim 1, wherein the metering time for the alcohol amounts to 10 minutes to 20 hours.

9. A process according to claim 1, wherein lithium tert-butoxide, lithium tert-amoxide or lithium isopropoxide are prepared in hexane or heptane-containing solvents.

10. A process according to claim 1, wherein the solvent is selected from the group consisting of pentane, hexane, heptane, octane and methyl cyclohexane.

11. A process according to claim 1, wherein the solvent comprises hexane.

12. A process according to claim 1, wherein the solvent is on industrial section step selected from the group consisting of an industrial hexane, paraffin oil, benzene, toluene, ethyl benzene, xylene and cumene.

13. A process according to claim 1, wherein the solvent is selected from the group consisting of diethyl ether, methyl tert-butyl ether, dipropyl ether, dibutyl ether and diphenyl ether.

14. A process according to claim 1, wherein the solvent comprises at least one member is selected from the group consisting of diethyl ether, methyl tert-butyl ether, dipropyl ether, dibutyl ether and diphenyl ether.

* * * * *